(12) United States Patent
Guo et al.

(10) Patent No.: US 11,266,229 B2
(45) Date of Patent: Mar. 8, 2022

(54) STERILIZABLE FACIAL CLEANING INSTRUMENT

(71) Applicant: GUANGDONG BAISHENGTU TECHNOLOGY CO. LTD, Foshan (CN)

(72) Inventors: Jiangang Guo, Foshan (CN); Peng Ma, Foshan (CN); Hou Xiong, Foshan (CN)

(73) Assignee: GUANGDONG BAISHENGTU TECHNOLOGY CO. LTD., Foshan (CN)

( * ) Notice: Subject to any disclaimer, the term of this patent is extended or adjusted under 35 U.S.C. 154(b) by 335 days.

(21) Appl. No.: 16/578,312

(22) Filed: Sep. 21, 2019

(65) Prior Publication Data
US 2020/0315339 A1  Oct. 8, 2020

(30) Foreign Application Priority Data

Apr. 4, 2019 (CN) .......................... 201910271278.5
Apr. 4, 2019 (CN) .......................... 201920460125.0

(51) Int. Cl.
*A46B 17/06* (2006.01)
*A46B 13/00* (2006.01)
(Continued)

(52) U.S. Cl.
CPC .......... *A46B 17/065* (2013.01); *A46B 13/001* (2013.01); *A46B 13/008* (2013.01);
(Continued)

(58) Field of Classification Search
CPC ..... A46B 13/008; A46B 13/02; A46B 17/065; A46B 2200/1006; A61L 2/10; A61L 2202/11
See application file for complete search history.

(56) References Cited

U.S. PATENT DOCUMENTS

| 2013/0047357 A1* | 2/2013 | Diaz | A46B 11/002 |
| | | | 15/104.94 |
| 2015/0313354 A1* | 11/2015 | Mongan | A46B 17/06 |
| | | | 15/22.1 |

(Continued)

FOREIGN PATENT DOCUMENTS

| CN | 206342119 | 7/2017 |
| CN | 207928572 | 10/2018 |

(Continued)

OTHER PUBLICATIONS

International Search Report of PCT/CN2019/095948 Completed Dec. 6, 2019; dated Dec. 31, 2019 4 pages.

(Continued)

*Primary Examiner* — Randall E Chin
(74) *Attorney, Agent, or Firm* — The Roy Gross Law Firm, LLC; Roy Gross

(57) ABSTRACT

Disclosed is a sterilizable facial cleaning instrument, which comprises a main apparatus, and a driving motor, a first control board and a rechargeable battery that are provided in the main apparatus, and further comprises an apparatus seat provided with a sterilization cavity, wherein an ultraviolet germicidal lamp is provided in the sterilization cavity; the main apparatus is detachably provided at the apparatus seat and at least a part of a brush head is positioned in the sterilization cavity, so that bristles positioned in the sterilization cavity can be sterilized by ultraviolet irradiation. The sterilizable facial cleaning instrument provided by the present invention can sterilize and disinfect the brush head completely when the main apparatus is combined with the separable designed apparatus seat, thereby ensuring the health and safety of users.

7 Claims, 2 Drawing Sheets

(51) Int. Cl.
  *A61L 2/10*   (2006.01)
  *A46B 13/02*  (2006.01)
(52) U.S. Cl.
  CPC ............. *A46B 13/02* (2013.01); *A61L 2/10* (2013.01); *A46B 2200/1006* (2013.01); *A61L 2202/11* (2013.01)

(56) References Cited

U.S. PATENT DOCUMENTS

2016/0302567 A1    10/2016  Gorelick
2017/0332850 A1*   11/2017  Powell ................... B08B 1/002
2020/0022489 A1*    1/2020  Schroeder .............. A46B 17/06

FOREIGN PATENT DOCUMENTS

CN    109200311    1/2019
CN    208464704    2/2019
CN    109907478    6/2019

OTHER PUBLICATIONS

Written Opinion of PCT/CN2019/095948 Completed Dec. 6, 2019; dated Dec. 31, 2019 5 pages.
Translation of International Search Report of PCT/CN2019/095948 Completed Dec. 6, 2019; dated Dec. 31, 2019 3 pages.

* cited by examiner

STERILIZABLE FACIAL CLEANING INSTRUMENT

TECHNICAL FIELD

The invention relates to a small-sized electric appliance, in particular to a sterilizable facial cleaning instrument.

BACKGROUND OF THE INVENTION

The facial cleaning instrument is also called as a face washing brush, which mainly uses an electric machine to drive the brush head or uses the ultrasonic principle to vibrate the fine bristles on the face washing brush, thus achieving high-efficiency and non-irritating cleaning and massage effects, which can help facial cleanser to form uniform foam of high-density, clean a face thoroughly, and achieve the effects of beauty and health care. At present, general facial cleaning instruments adopt rechargeable structures. Taking motor drive as an example, a facial cleaning instrument usually includes a main apparatus, and a driving motor, a control board and a rechargeable battery that are provided in the main apparatus. The main apparatus is provided with a charging interface that is electrically connected to the control board to charge the rechargeable battery. The output end of the driving motor is connected with a brush head on which bristles are provided. In operation, firstly a face can be wetted with clean water, or further cooperating with facial cleanser, and uniform foam of high-density is formed due to bristles vibrated by the facial cleaning instrument, cleaning the face thoroughly. However, the bristles on the current brush head are prone to breed bacteria. Although silica gel brush head can alleviate this problem to some extent, it cannot be avoided thoroughly. The brush head still needs to be disinfected regularly, which is very inconvenient to use.

SUMMARY OF THE INVENTION

In view of the above problems existing in the prior art, the present invention aims to provide a sterilizable facial cleaning instrument that can sterilize the brush head of the facial cleaning instrument conveniently.

In order to achieve the above purpose, the sterilizable facial cleaning instrument provided by the present invention comprises a main apparatus, and a driving motor, a first control board and a rechargeable battery that are provided in the main apparatus, wherein the main apparatus is provided with a first charging component that is electrically connected to the first control board so as to charge the rechargeable battery, an output end of the driving motor is connected with a brush head on which bristles are provided, wherein an apparatus seat provided with a sterilization cavity is also included, an ultraviolet germicidal lamp is provided in the sterilization cavity, the main apparatus is detachably provided at the apparatus seat, and at least a part of the brush head is positioned in the sterilization cavity, so that the bristles positioned in the sterilization cavity can be sterilized by ultraviolet irradiation.

Preferably, the main apparatus is provided with a key switch for controlling the working state of the sterilizable facial cleaning instrument and a first induction switch for realizing sterilization operation; a second control board, a power input end and a second induction switch triggered by the first induction switch to control the ultraviolet germicidal lamp are provided in the apparatus seat.

Preferably, a second charging component is further provided on the apparatus seat, and the second charging component fits the first charging component, and the second control board is configured to control the ultraviolet germicidal lamp to perform sterilization operation and control the second charging component to charge the rechargeable battery through the first charging component when the second induction switch is triggered.

Preferably, the apparatus seat comprises a base, one side of which is provided with a support arm, an end of the support arm is provided with a horizontal cantilever, and the second induction switch and/or the second charging component are provided on the cantilever; correspondingly, when the main apparatus is combined with the apparatus seat, the first induction switch and the first charging component correspond to the positions of the second induction switch and the second charging component, respectively.

Preferably, the sterilization cavity is provided on the base, and the top of the sterilization cavity is provided with an opening which can be snap-fitted with the brush head.

Preferably, the periphery of the brush head is provided with a step surface which is snap-fitted with the opening.

Preferably, a heat generating element is further provided in the sterilization cavity, the heat generating element is electrically connected to the second control board, and the second control board is further configured to control the heat generating element to generate heat so as to dry the bristles when the second induction switch is triggered.

Preferably, the heat generating element is horizontally embedded in the sterilization cavity and is provided with an opening thereon, and the ultraviolet germicidal lamp is disposed through the opening.

Preferably, the second control board is provided with a timing module which is configured to cut off a power supply of the ultraviolet germicidal lamp and/or the heat generating element according to a preset time.

Preferably, the bristles are made of animal hair or silica gel.

Compared with the prior art, the sterilizable facial cleaning instrument provided by the prevent invention can sterilize and disinfect the brush head completely when the main apparatus is combined with the separable designed apparatus seat, thus ensuring the health and safety of the users. At the same time, in a further improvement solution, through the cooperation between the first charging component and the second charging component, the main apparatus can be charged while sterilizing is performed.

It is understood that both the foregoing general description and the following detailed description are exemplary and explanatory only, and are not intended to limit the disclosure.

This application document provides an overview of various embodiments or examples of the technique described in this disclosure, rather than the whole scope of disclosed technique or full disclosure of all of features.

1—main apparatus; 2—apparatus seat; 11—first control board; 12—rechargeable battery; 13—brush head; 14—driving motor; 15—key switch; 21—second control board; 22—heat generating element; 23—UV germicidal lamp; 24—power input end; 25—sterilization cavity; 26—base; 27—support arm; 28—cantilever; 111—first induction switch; 112—second induction switch; 113—second charging component; 114—first charging component; 131—bristles.

DETAILED DESCRIPTION OF EMBODIMENTS

In order to make the purposes, technical solutions and advantages of the embodiments of present disclosure clearer, the following will describe the technical solutions of the embodiments of present disclosure clearly and completely with reference to the drawings of the embodiments of present disclosure. Obviously, the described embodiments are parts of embodiments of the present disclosure instead of all of embodiments. On the basis of the described embodiments of the present disclosure, all of other embodiments obtained by a person of ordinary skill in the art without inventive work are within the protection scope of the present disclosure.

Unless otherwise defined, the technical terms or scientific terms used in the present disclosure shall have the ordinary meaning that is understood by those with ordinary skills in the art to which this disclosure belongs. As used in this disclosure, similar words such as "include" or "comprise" mean that the elements or articles appearing before the word cover the elements or articles and their equivalents listed after the word, but not excluding other elements or articles. Similar words such as "connect" are not limited to physical or mechanical connections, but may also include electrical connections, whether direct or indirect. "Up", "down", "left" and "right" are only used to indicate the relative positional relationship. When the absolute position of the described object is changed, the relative positional relationship may also be changed accordingly.

In order to keep the following description of the embodiments of present disclosure clear and concise, detailed descriptions of known functions and known components are omitted from the present disclosure.

Figure 1:
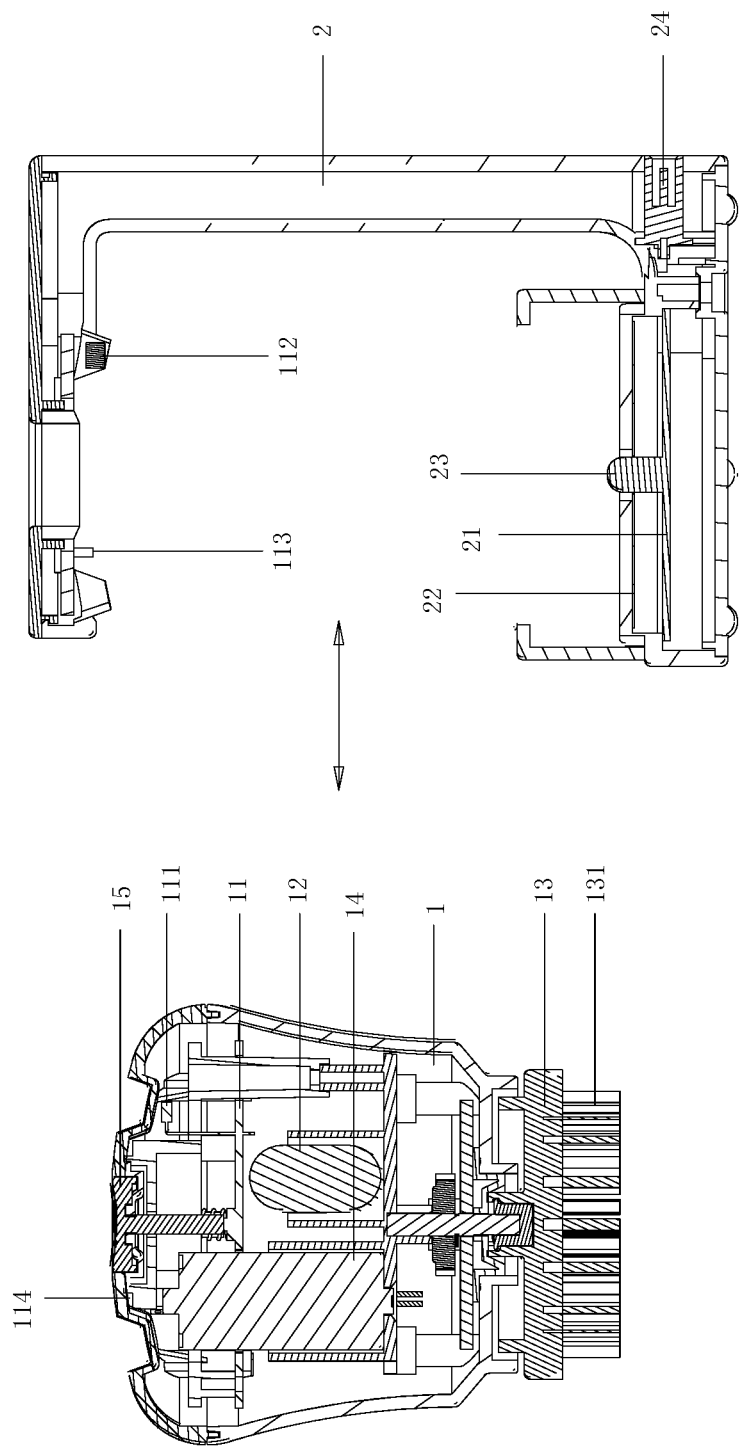
FIG. 1 is a structurally schematic diagram when the main apparatus and the apparatus seat of the sterilizable facial cleaning instrument of the present invention are separated.
Figure 2:
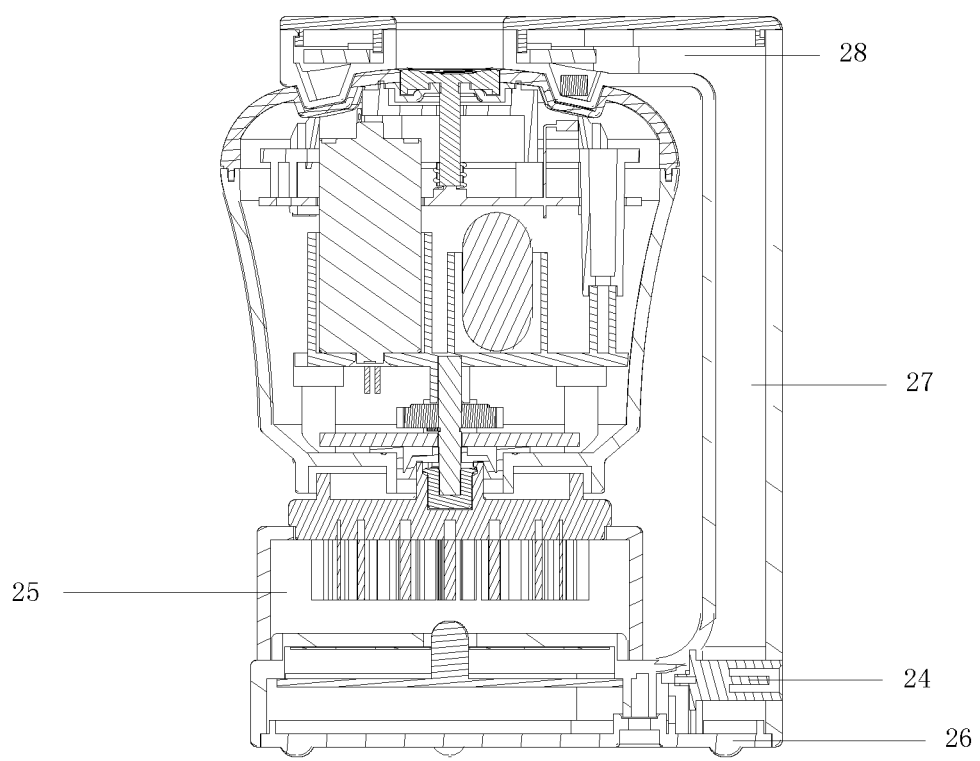
FIG. 2 is a structurally schematic diagram when the main apparatus and the apparatus seat of the sterilizable facial cleaning instrument of the present invention are combined.

As shown in FIGS. 1 and 2, the sterilizable facial cleaning instrument provided by the present invention comprises a main apparatus 1, and a driving motor 14, a first control board 11 and a rechargeable battery 12 that are provided in the main apparatus 1, wherein the main apparatus 1 is provided with a first charging component 114 that is electrically connected to the first control board 11 so as to charge the rechargeable battery 12, an output end of the driving motor 14 is connected with a brush head 13, and bristles 131 are provided on the brush head 13, wherein, the sterilizable facial cleaning instrument further comprises an apparatus seat 2 provided with a sterilization cavity 25 in which an ultraviolet germicidal lamp 23 is provided, the main apparatus 1 is detachably provided at the apparatus seat 2, and at least a part of the brush head 13 is positioned in the sterilization cavity 25, so that the bristles positioned in the sterilization cavity 25 can be sterilized by ultraviolet irradiation. The sterilizable facial cleaning instrument provided by the embodiment of the present invention can realize the sterilization and disinfection of the brush head completely when the main apparatus is combined with the separable designed apparatus seat, thereby ensuring the health and safety of the users.

In a further improvement solution, since the main apparatus 1 is generally held by a user to complete the face cleaning operation, it is generally necessary to provide a key switch on the main apparatus. As shown in FIG. 1, in the present invention, similarly, it is preferable that the main apparatus 1 is provided with a key switch 15 for controlling the working state of the sterilizable cleaning instrument. However, at the same time, a first induction switch 111 for triggering the sterilization operation may also be provided in this embodiment; in this situation, a second control board 21, a power input end 24, and a second induction switch 112 triggered by the first induction switch 111 to control the ultraviolet germicidal lamp 23 are provided in the apparatus seat 2. As shown in the figures, the ultraviolet germicidal lamp 23 and the second control board 21 are electrically connected and positioned in the sterilization cavity 25, and the first induction switch 111 is provided on the main apparatus 1. Therefore, when the main apparatus 1 is combined with the apparatus seat 2, the second induction switch 112 corresponding to the position of the first induction switch 111 will be triggered to form a control loop, thereby realizing the control of the ultraviolet germicidal lamp 23 by the second control board 21.

In the present invention, the first charging component 114 is provided on the main apparatus 1, and its function is to realize the charging operation of the rechargeable battery 12 of the main apparatus 1 from outside. Therefore, the first charging component may actually be a conventional charging interface, such as an AC interface, an USB interface, a mircoUSB, a miniUSB or a TypeC interface, etc. Correspondingly, as shown in FIG. 1, in some preferred embodiments, it is preferable that the apparatus seat 2 is further provided with a second charging component 113, which fits the first charging component 114, and the second control board 21 is configured to control the ultraviolet germicidal lamp 23 to perform sterilization operation, and control the second charging component 113 to charge the rechargeable battery 12 through the first charging component 114 when the second induction switch 112 is triggered. As can be conceivable, in this embodiment, the second charging component 113 is actually an interface forming a fit relationship with the first charging component. For example, when the first charging component 114 is a TypeC female joint, the second charging component 113 should be a TypeC male joint.

In a still further preferred embodiment, as shown in FIGS. 1 and 2, the apparatus seat 2 preferably includes a base 26, one side of which is provided with a support arm 27, an end of the support arm 27 is provided with a horizontal cantilever 28, and the second induction switch 112 and/or the second charging component 113 are provided on the cantilever 28; correspondingly, when the main apparatus 1 is combined with the apparatus seat 2, the first induction switch 111 and the first charging component 114 correspond to the positions of the second induction switch 112 and the second charging component 113 respectively. In other words, when the apparatus seat 1 is combined with the apparatus seat 2, the main apparatus 1 can be charged through the second control board 21, and the operation of the ultraviolet germicidal lamp 23 may be controlled simultaneously so as to disinfect the bristles 131 of the brush head 13 on the main apparatus 1 with ultraviolet rays.

With continued reference to FIG. 1, in some embodiments, the sterilization cavity 25 is disposed on the base 26, and the top of the sterilization cavity 25 has an opening (not marked in the figure) that is snap-fitted with the brush head 13. At this time, since the brush head 13 is partially inserted into the sterilization cavity 25, in fact, the sterilization cavity 25 also plays a role of supporting the main apparatus 1 as a whole. In order to ensure the stability of support, as shown in FIG. 1, the periphery of the brush head 13 is provided with a stepped surface (not marked in the figure) that is snap-fitted with the opening.

As can be conceivable, for the facial cleaning instrument, the brush head 13 is used as a component that directly contacts the skin, and also needs to contact liquids such as water and facial cleanser. The brush head 13 must be cleaned after a facial cleaning operation. If water is not wiped or dried, bacteria are prone to grow. Therefore, as shown in FIG. 1, preferably, a heat generating element 22 is provided in the sterilization cavity 25, the heat generating element 22 is electrically connected to the second control board 21, which is further configured to control the heat generating element 22 to generate heat so as to dry the bristles 131 when the second induction switch 112 is triggered.

In some embodiments, it is preferable that the heat generating element 22 is horizontally embedded in the sterilization cavity 25, an opening (not marked in FIG. 1) is formed on the heat generating element 22, and the ultraviolet germicidal lamp 23 is disposed through the opening. In this way, the brush head 13 and/or bristles 131 can be dried while ultraviolet sterilization is performed.

As mentioned above, in one or more embodiments of the present invention as proposed above, the charging, drying, sterilization and disinfection of the facial cleaning instrument can be achieved separately or simultaneously, which mainly depends on the control of the first control board 11 or the second control board 21. In order to realize more accurate control, in some embodiments, the second control board 21 is preferably provided with a timing module which is configured to cut off a power supply of the ultraviolet germicidal lamp 23 and/or the heat generating element 22 according to a preset time.

In addition, for the brush head 13 of the above-mentioned facial cleaning instrument of the present invention, in order to realize drying and disinfection effects better, the bristles 131 are preferably made of animal hair or silica gel.

The above embodiments are merely exemplary embodiments of the present invention and are not intended to limit the present invention. The protection scope of the present invention is defined by the claims. A person skilled in the art can make various modifications or equivalent substitutions within the essence and scope of the present invention, and such modifications or equivalent substitutions should also be regarded as falling within the scope of the present invention.

The invention claimed is:

1. A sterilizable facial cleaning instrument, which comprises a main apparatus, and a driving motor, a first control board and a rechargeable battery that are provided in the main apparatus, wherein the main apparatus is provided with a first charging component electrically connected to the first control board to charge the rechargeable battery, an output end of the driving motor is connected with a brush head, and bristles are provided on the brush head, characterized in that:
further comprises an apparatus seat provided with a sterilization cavity, in which an ultraviolet germicidal lamp is provided, the main apparatus is detachably provided at the apparatus seat, and at least a part of the brush head is positioned in the sterilization cavity, so that bristles positioned in the sterilization cavity can be sterilized by ultraviolet irradiation, wherein
the main apparatus is provided with a key switch for controlling the working state of the sterilizable facial cleaning instrument and a first induction switch for realizing sterilization operation; a second control board, a power input end and a second induction switch triggered by the first induction switch to control the ultraviolet germicidal lamp are provided in the apparatus seat;
the apparatus seat is further provided with a second charging component which fits the first charging component, and the second control board is configured to control the ultraviolet germicidal lamp to perform sterilization operation and control the second charging component to charge the rechargeable battery through the first charging component when the second induction switch is triggered; and
the apparatus seat comprises a base, one side of which is provided with a support arm, an end of the support arm is provided with a horizontal cantilever, and the second induction switch and/or the second charging component are provided on the cantilever; correspondingly, when the main apparatus is combined with the apparatus seat, the first induction switch and the first charging component correspond to the positions of the second induction switch and the second charging component, respectively.

2. The sterilizable facial cleaning instrument according to claim 1, characterized in that, the sterilization cavity is provided on the base, and the top of the sterilization cavity is provided with an opening that is snap-fitted with the brush head.

3. The sterilizable facial cleaning instrument according to claim 2, characterized in that, the periphery of the brush head is provided with a step surface that is snap-fitted with the opening.

4. The sterilizable facial cleaning instrument according to claim 1, characterized in that, a heat generating element is further provided in the sterilization cavity, and the heat generating element is electrically connected to the second control board, wherein the second control board is further configured to control the heat generating element to generate heat so as to dry the bristles when the second induction switch is triggered.

5. The sterilizable facial cleaning instrument according to claim 4, characterized in that, the heat generating element is horizontally embedded in the sterilization cavity and is provided with an opening, the ultraviolet germicidal lamp is disposed through the opening.

6. The sterilizable facial cleaning instrument according to claim 4, characterized in that, a timing module is provided on the second control board, wherein the timing module is configured to cut off a power supply of the ultraviolet germicidal lamp and/or the heat generating element according to a preset time.

7. The sterilizable facial cleaning instrument according to claim 1, characterized in that, the bristles are made of animal hair or silica gel.

* * * * *